(12) United States Patent
Tani

(10) Patent No.: US 11,390,897 B2
(45) Date of Patent: Jul. 19, 2022

(54) METHOD FOR PRODUCING ERGOTHIONEINE

(71) Applicant: National University Corporation Okayama University, Okayama (JP)

(72) Inventor: Akio Tani, Okayama (JP)

(73) Assignee: National University Corporation Okayama University, Okayama (JP)

( * ) Notice: Subject to any disclaimer, the term of this patent is extended or adjusted under 35 U.S.C. 154(b) by 1008 days.

(21) Appl. No.: 16/314,102

(22) PCT Filed: Dec. 21, 2015

(86) PCT No.: PCT/JP2015/085698
§ 371 (c)(1),
(2) Date: Mar. 21, 2019

(87) PCT Pub. No.: WO2016/104437
PCT Pub. Date: Jun. 30, 2016

(65) Prior Publication Data
US 2021/0164004 A1  Jun. 3, 2021

(30) Foreign Application Priority Data

Dec. 22, 2014 (JP) .............................. JP2014-259232
Aug. 6, 2015 (JP) .............................. JP2015-156037

(51) Int. Cl.
C12P 17/10 (2006.01)
C12N 9/16 (2006.01)
C12P 13/04 (2006.01)
C12N 1/20 (2006.01)

(52) U.S. Cl.
CPC .............. *C12P 17/10* (2013.01); *C12N 1/205* (2021.05); *C12P 13/04* (2013.01)

(58) Field of Classification Search
CPC ... C12N 9/16; C12N 1/14; C12N 1/16; C12N 2800/30; C12P 17/10; C12P 17/04; C12P 7/24; C12Y 201/01; C12Y 401/02004
USPC ........... 435/252.1, 255.1, 375, 410; 504/117; 514/183, 277, 456, 369
See application file for complete search history.

(56) References Cited

U.S. PATENT DOCUMENTS

| | | | |
|---|---|---|---|
| 5,438,151 A | 8/1995 | Yadan et al. | |
| 2011/0028321 A1 | 2/2011 | Tani et al. | |

FOREIGN PATENT DOCUMENTS

| | | |
|---|---|---|
| JP | 2006-160748 A | 6/2006 |
| JP | 2012-105618 A | 6/2012 |
| JP | 5394259 B2 | 1/2014 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
D. S. Genghof, "Biosynthesis of Ergothioneine and Hercynine by Fungi and Actinomycetales," Journal of Bacteriology, vol. 103, No. 2, Aug. 1970, pp. 475-478. (cited in the ISR).
T. Pluskal, "Genetic and Metabolomics Dissection of the Ergothioneine and Selenoneine Biosynthetic Pathway in the Fission Yeast, S. pombe, and Construction of an Overproduction System," PLOS One. 2014; vol. 9, Issue 5, e97774, pp. 1-12. (cited in the ISR and discussed in the spec).
D. S. Genghof, "Biosynthesis of Ergothioneine and Hercynine By Mycobacteria," Journal of Bacteriology, 1964, vo. 87, No. 4, pp. 852-862. (cited in the ISR).
S. L. Forsburg et al., "Basic Methods for Fission Yeast," Yeast, vol. 23, No. 3, Feb. 2006, p. 173-183. (cited in the ISR).
K. M. Alamgir, "Production of Ergothioneine by Methylobacterium Species," Frontiers in Microbiology, Oct. 2015, vol. 6, article 1185, pp. 1-12. (cited in the ISR).
D. B. Melville et al., "Ergothioneine in Microorganisms," J. Biol Chem. 1956, 223: 9-17 and information sheet. (discussed in the spec).
F. P. Seebeck, "In Vitro Reconstitution of Mycobacterial Ergothioneine Biosynthesis," J Am Chem Soc. May 19, 2010;132(19), pp. 6632-6633, S1-S14 and graphs (3 sheets) (discussed in the spec).
T. Nakagawa et al., "A Catalytic Role of XoxF1 as La3+ -Dependent Methanol Dehydrogenase in Methylobacterium extorquens Strain AM1," Plos One, vol. 7, No. 11, 2012, e50480, pp. 1-7. (discussed in the spec).
Lennart Schada von Borzyskowski et al., "An engineered Calvin-Benson-Bassham cycle for carbon dioxide fixation in Methylobacterium extorquens AM1" Metabolic Engineering 47, 2018, pp. 423-433. (discussed in the spec).
Elizabeth Skovran, et al., "XoxF Is Required for Expression of Methanol Dehydrogenase in Methylobacterium extorquens AM1," Journal of Bacteriology, vol. 193, No. 21, Nov. 2011, pp. 6032-6038. (discussed in the spec).
International Preliminary Report on Patentability dated Jul. 27, 2016, issued for PCT/JP2015/085698.
International Search Report dated Feb. 2, 2016, issued for PCT/JP2015/085698.

* cited by examiner

*Primary Examiner* — Robert B Mondesi
*Assistant Examiner* — Mohammad Y Meah
(74) *Attorney, Agent, or Firm* — Locke Lord LLP

(57) ABSTRACT

The present invention relates to a method including culturing a $C_1$ compound-assimilating bacterium, which is a methylotroph, and/or a yeast by using a medium comprising, for example, a $C_1$ compound and/or glycerol as a carbon source, to thereby produce EGT.

18 Claims, 18 Drawing Sheets

SDS-PAGE analysis of samples (0.28 mg/ml of proteins)
1, 5 µL; 2, 10 µL; 3, 15 µL

METHOD FOR PRODUCING ERGOTHIONEINE

TECHNICAL FIELD

The present invention relates to a production method and manufacturing method for ergothioneine, and more specifically, to a production method and manufacturing method for ergothioneine using a $C_1$ compound-assimilating bacterium and/or a yeast. The present application claims priority from Japanese Patent Application No. 2014-259232 and Japanese Patent Application No. 2015-156037, which are incorporated herein by reference.

Methylobacterium Strains described below are deposited with National Institute of Technology and Evaluation (NITE), which is an International Depository Authority under the provisions of the Budapest Treaty. The Accession Numbers of the *Methylobacterium* strains are, respectively, NITE BP-02088, NITE BP-02089, and NITE BP-02090. The budding yeasts of *Rhodotorula* strain are deposited with NITE with accession numbers, respectively, NITE BP-02171 and NITE BP-02172.

BACKGROUND ART

Ergothioneine is a kind of amino acid and has high antioxidant activity. However, much remains to be known about its biological role. Ergothioneine can rapidly scavenge hydroxy radicals, and hence is considered to be involved in removal of active oxygen in cells. Ergothioneine is biosynthesized from histidine, and its sulfur atom is supplied from cysteine. However, ergothioneine is not synthesized in the body of a mammal, and hence needs to be ingested from an outside source.

As a manufacturing method for ergothioneine, for example, there are known: a chemical synthesis method; a method involving culturing an ascomycete or basidiomycete that produces ergothioneine, and then extracting and purifying ergothioneine; a fermentation method; and a method involving extracting ergothioneine from animal blood or the like containing ergothioneine. However, there is not very much information about organisms that produce ergothioneine. There is only a report on production of ergothioneine in limited molds, mushrooms, and bacteria (Non Patent Literature 1), and information about organisms that accumulate large amounts of ergothioneine is further limited.

As another method, there is a report that ergothioneine extracted from the golden oyster mushroom (*Pleurotus cornucopiae* var. *citrinopileatus*) reaches a production amount of 450 mg/L under optimal conditions (Patent Literature 1). The method described in Patent Literature 1 exhibits high productivity, but is considered to still have problems with cost and the like because of a long culture time, use of an organic solvent in extraction from cells of the fungus, and supplementation of a medium with methionine. In addition, ergothioneine obtained by a chemical synthesis method described in Patent Literature 2 still has problems such as an expensive synthesis reagent and costly purification. With regard to production of ergothioneine in molds, mushrooms, and bacteria, there is no report of a production amount surpassing that achieved by the method described in Patent Literature 1.

In recent years, a biosynthesis pathway of ergothioneine has been elucidated in the bacterium of the genus *Mycobacterium*, and it has been reported that genes involved therein are conserved across a wide range of microorganisms (Non Patent Literature 2). Clustered egtABCDE genes have been found in the *Mycobacterium* sp. bacteria as ergothioneine synthesis genes, and homologous genes for egtB and egtD have also been found in many eukaryotes and bacteria including the bacterium of the genus *Methylobacterium* The egtABCDE genes are genes encoding proteins that convert histidine to ergothioneine. However, whether microorganisms having those genes, such as the bacterium of the genus *Methylobacterium*, actually have an ergothioneine-synthesizing ability, and ergothioneine productivity of those microorganisms have yet to be elucidated.

Among microorganisms, there are $C_1$ compound-assimilating bacteria (methylotrophs), which utilize a compound containing only one carbon atom as a carbon source. Examples of the $C_1$ compound serving as a metabolic starting material for the $C_1$ compound-assimilating bacteria include methanol and methylamine (methyl amine). With regard to the $C_1$ compound-assimilating bacteria, there is no report on biosynthesis of ergothioneine. The bacterium of the genus *Methylobacterium* have been reported as microorganisms that are $C_1$ compound-assimilating bacteria (Patent Literature 3). The bacterium of the genus *Methylobacterium* are gram-negative bacteria capable of utilizing methanol as a sole carbon source, and are often found on plant surfaces. Progress has been made in researching a methanol metabolic pathway using *M. extorquens* strain AM1 as a model. The bacterium of the genus *Methylobacterium* have methanol dehydrogenases MxaF and XoxF (Non Patent Literature 3). In Non Patent Literature 3, it is reported that an MxaF-disrupted strain cannot grow on methanol in a general medium, but grows in the presence of lanthanum, a rare earth element. This is because XoxF is a methanol dehydrogenase containing lanthanum as a prosthetic group (Non Patent Literature 4). Meanwhile, an XoxF gene-disrupted strain of strain AM1 exhibits reduced growth on methanol in the presence of calcium, suggesting that expression of MxaF requires XoxF1 (Non Patent Literature 5).

In addition, there is a report that metabolomic analysis of a fission yeast *Schizosaccharomyces pombe* under a glucose-starved condition revealed production of ergothioneine as a metabolite (Non Patent Literature 6). However, detailed analysis has not been performed on an ergothioneine-synthesizing ability of a yeast, and there is no report particularly concerning ergothioneine synthesis by a budding yeast.

CITATION LIST

Patent Literature

[PTL 1] JP 2012-105618 A
[PTL 2] JP 2006-160748 A
[PTL 3] JP 5394259 B2

Non Patent Literature

[NPL 1] J. Biol. Chem. 1956, 223: 9-177
[NPL 2] J Am Chem Soc. 2010 May 19; 132(19): 6632-3
[NPL 3] PLoS ONE, 7, e50480 (2012) DOI: 10.1371/journal.pone.0050480
[NPL 4] J Biosci Bioeng, 111, 547-549 (2011) DOI: 10.1016/j.jbiosc.2010.12.017
[NPL 5] J Bacteriol, 193, 6032-6038 (2011) DOI: 10.1128/JB.05367-11
[NPL 6] PLoS One. 2014; 9(5): e97774. DOI: 10.1371/journal.pone.0097774

SUMMARY OF INVENTION

Technical Problem

An object of the present invention is to provide a highly safe method of easily producing and manufacturing ergothioneine (hereinafter referred to as "EGT").

Solution to Problem

The inventor of the present invention has made extensive investigations in order to achieve the above-mentioned object, and as a result, has found, through analysis of metabolites in cells of a $C_1$ compound-assimilating bacterium and/or a yeast by metabolomic analysis, that the $C_1$ compound-assimilating bacterium and/or the yeast can produce EGT. The inventor has found that, when a selected bacterium or yeast is cultured using a medium containing a $C_1$ compound or glycerol, EGT can be produced with the $C_1$ compound or glycerol serving as a carbon source, and hence the above-mentioned object can be achieved. Thus, the inventor has completed the present invention.

That is, the present invention includes the following.

1. A manufacturing method for ergothioneine, including a step of culturing a $C_1$ compound-assimilating bacterium and/or a yeast by using a medium comprising a carbon source, to thereby produce ergothioneine.

2. The manufacturing method for ergothioneine according to Item 1, wherein the manufacturing method includes a step of culturing the $C_1$ compound-assimilating bacterium and/or the yeast by using a medium comprising methanol, methylamine, and/or glycerol as the carbon source, to thereby produce ergothioneine.

3. The manufacturing method according to Item 1 or 2, wherein the $C_1$ compound-assimilating bacterium includes a bacterium of the genus *Methylobacterium*.

4. The manufacturing method according to any one of Items 1 to 3, wherein the yeast includes a yeast of a genus *Rhodotorula*.

5. The manufacturing method according to any one of Items 1 to 4, wherein the medium comprises the carbon source at a concentration of from 0.1% to 5%.

6. The manufacturing method according to any one of Items 1 to 5, wherein the medium comprises an ammonium salt at a concentration of from 0.2 g/L to 2.0 g/L.

7. The manufacturing method according to any one of Items 1 to 6, wherein the medium comprises ammonium chloride or ammonium dihydrogen phosphate as an ammonium salt.

8. A manufacturing method for ergothioneine, including the following steps:
1) a step of culturing a $C_1$ compound-assimilating bacterium and/or a yeast by the method of any one of Items 1 to 7; and 2) a step of subjecting the cultured $C_1$ compound-assimilating bacterium and/or yeast to heat treatment to extract the produced ergothioneine from the $C_1$ compound-assimilating bacterium and/or the yeast.

9. The manufacturing method for ergothioneine according to any one of Items 1 to 8, wherein the $C_1$ compound-assimilating bacterium includes a $C_1$ compound-assimilating bacterium selected from those of $C_1$ compound-assimilating the genus *Methylobacterium* respectively deposited under the accession numbers NITE BP-02088, NITE BP-02089, and NITE BP-02090.

10. The manufacturing method for ergothioneine according to any one of Items 1 to 9, wherein the yeast includes a yeast selected from yeasts of the genus *Rhodotorula* respectively deposited under the accession numbers NITE BP-02171 and NITE BP-02172.

Advantageous Effects of Invention

According to the method of producing EGT with the $C_1$ compound-assimilating bacterium and/or the yeast of the present invention, EGT can be accumulated in cells thereof in a culture time of 7 days through culture using, for example, the $C_1$ compound or glycerol as the carbon source. There is also no need to supplement the medium for culturing the cells with methionine. In addition, EGT can be easily extracted from the cells by subjecting the cultured bacterium and/or yeast to heat treatment, and hence EGT can be produced, purified, and manufactured simply and safely without the need to disrupt the cells or use an organic solvent.

DESCRIPTION OF EMBODIMENTS

Figure 1:
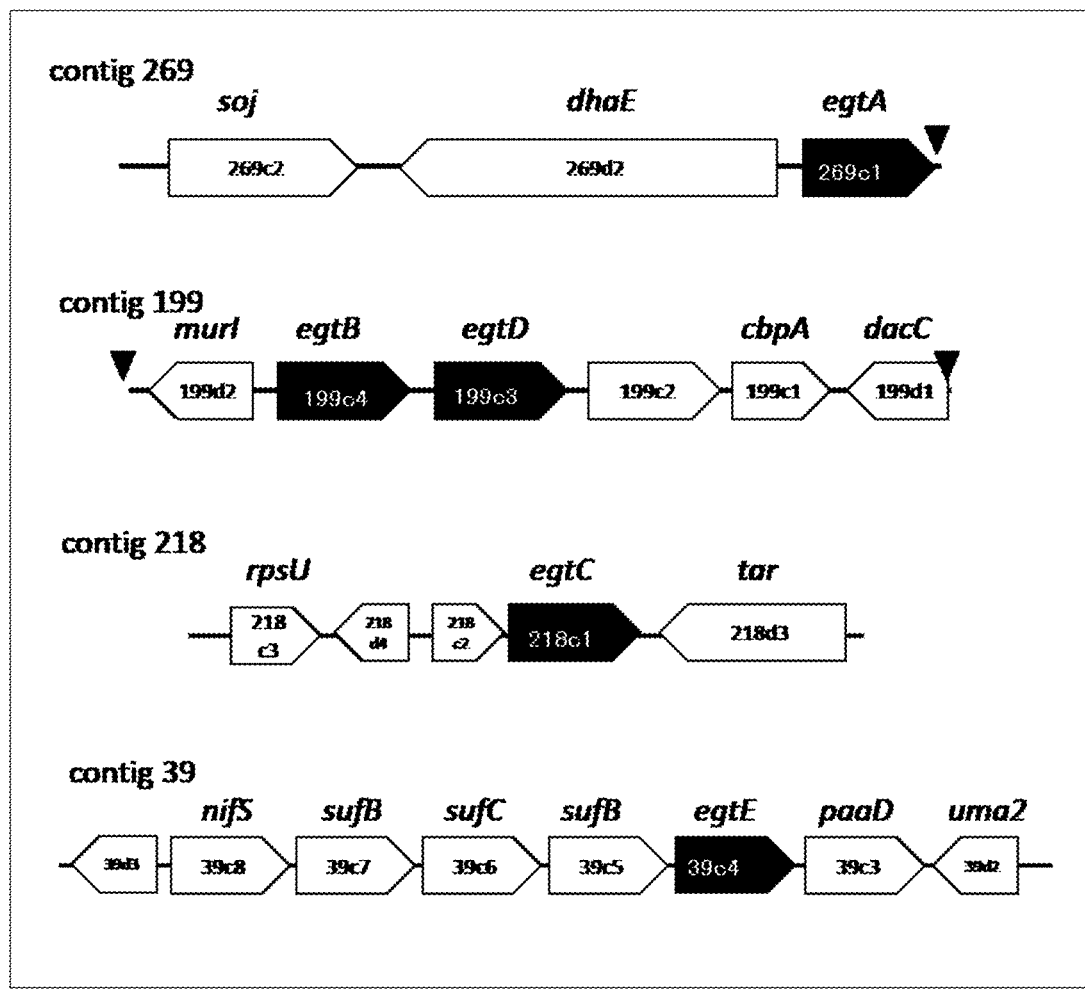
FIG. 1 is a diagram for illustrating the arrangement of genes (egtABCED) involved in EGT production, on the genome of *M. aquaticum* strain MA-22A.

The present invention relates to a production method and manufacturing method for EGT including culturing a $C_1$ compound-assimilating bacterium and/or a yeast by using a medium containing a carbon source, such as methanol ($CH_3OH$), methylamine ($CH_3NH_2$), and/or glycerol ($C_3H_5(OH)_3$). Herein, EGT refers to a kind of amino acid represented by the following formula (I).

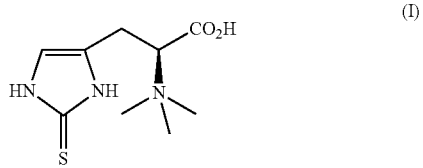

(I)

EGT may be manufactured by including a step of culturing a $C_1$ compound-assimilating bacterium and/or a yeast by using a medium containing a carbon source, such as methanol, methylamine, and/or glycerol, to thereby produce EGT in cells. Further, through heat treatment of the $C_1$ compound-assimilating bacterium and/or the yeast having the produced EGT in the cells thereof, EGT can be extracted from the $C_1$ compound-assimilating bacterium and/or the yeast. After the extraction step, the obtained EGT may be purified.

Herein, the "$C_1$ compound-assimilating bacterium" refers to a bacterium having a property of assimilating (assimilating bacterium) a compound containing only one carbon atom (e.g., methanol and/or methylamine), and more suitably refers to a methanol-assimilating bacterium. Genes and enzymes involved in a methanol metabolic pathway vary for different bacteria, but in many cases, methanol is oxidized to carbon dioxide to provide energy, and formaldehyde or carbon dioxide is fixed to synthesize constituent components of bacterial cells. Methanol has the simplest molecular structure among a series of alcohols, and is an inexpensive feedstock having the potential to serve as a non-food-competing carbon source. Methanol can be industrially produced with ease by using, for example, a copper oxide-zinc oxide/alumina composite oxide as a catalyst for carbon monoxide (CO) manufactured by partial oxidation of coal or natural gas. The "$C_1$ compound-assimilating bacterium" in the invention in this description encompasses a bacterium that can also utilize a carbon source other than the $C_1$ compound as well.

Herein, specific examples of the $C_1$ compound-assimilating bacterium include bacterium of the genus *Methylobacterium*. Examples of the bacterium of the genus *Methylobacterium* include *M. aquaticum*, *M. oryzae*, *M. extorquens*, *M. radiotolerans*, *M. nodulans*, *M. extorquens*, *M. brachiatum*, *M. adhaesivum*, *M. aerolatum*, *M. aminovorans*, *M. cerastii*, *M. fujisawaense*, *M. hispanicum*, *M. komagatae*, *M. marchantiae*, *M. oxalidis*, *M. populi*, *M. rhodesianum*, *M. rhodinum*, *M. soli*, *M. tardum*, *M. thiocyanatum*, and *M. zatmanii*. The $C_1$ compound-assimilating bacterium in the present invention is an aerobic bacterium. A bacterium selected from the following is more preferred: *M. aquaticum* strain MA-22A (bacterium identified by international accession number FERM BP-11078, converted to an international deposit under the Budapest Treaty from FERM P-21449 deposited on Nov. 28, 2007 (domestic accession date), in the International Patent Organism Depositary, National Institute of Advanced Industrial Science and Technology (Central 6, 1-1-1 Higashi, Tsukuba, Ibaraki 305-8566, Japan)), *M. brachiatum* strain 99d, *M. brachiatum* strain zlb, and *M. brachiatum* strain zle (bacteria identified by accession numbers NITE BP-02088, NITE BP-02089, and NITE BP-02090, respectively, converted to an international deposit under the Budapest Treaty from NITE P-02088, NITE P-02089, and NITE P-02090 deposited on Jul. 15, 2015 (domestic accession date), in NITE Patent Microorganisms Depositary (room 112, 2-5-8 Kazusakamatari, Kisarazu-shi, Chiba)).

Herein, the "yeast" is not particularly limited as long as the yeast can produce ergothioneine in the presence of a carbon source. Herein, the yeast is preferably a budding yeast. The yeast is more preferably an imperfect yeast, and specific examples thereof include yeasts of the genus *Rhodotorula* and the genus *Cryptococcus*. Examples of the yeast of the genus *Rhodotorula* include *Rhodotorula mucilaginosa* and *Rhodotorula glutinis*. A yeast selected from the following is more preferred: *Rhodotorula mucilaginosa* z41c and *Rhodotorula mucilaginosa* z41d (yeasts identified by accession numbers NITE BP-02171 and NITE BP-02172, respectively, internationally deposited to NITE Patent Microorganisms Depositary (room 112, 2-5-8 Kazusakamatari, Kisarazu-shi, Chiba) on Dec. 4, 2015 under the Budapest Treaty). In addition, examples of the yeast of the genus *Cryptococcus* include *Cryptococcus flavescens*, *Cryptococcus phenolicus*, and *Cryptococcus terreus*.

With regard to the carbon source in the medium in the present invention, the medium needs to contain a carbon source that can be utilized by the $C_1$ compound-assimilating bacterium and/or the yeast of the present invention, for example, the bacterium of the genus *Methylobacterium* and/or the yeast of the genus *Rhodotorula*. The carbon source is, for example, a $C_1$ to $C_5$ compound, preferably a $C_1$ to $C_3$ compound. In addition, the carbon source is preferably a $C_1$ to $C_5$ alcohol, carboxylic acid, ester, amine, or chloride, more preferably a $C_1$ to $C_5$ alcohol or amine. Specific examples of the $C_1$ to $C_5$ compound include methanol, methylamine, glycerol, ethanol, lactic acid, isoamyl alcohol, methylacetic acid, dichloromethane, pyruvic acid, and fumaric acid. In the present invention, it is more preferred that the medium contain a $C_1$ compound and/or glycerol as the carbon source. Specific examples of the $C_1$ compound include methanol and/or methylamine, and a suitable example is methanol. The medium contains the carbon source at a concentration of from 0.1% to 5%, preferably from 0.5% to 3%, most preferably about 2%. As described above, methanol is an inexpensive feedstock having the potential to serve as a non-food-competing carbon source. In addition, glycerol is an inexpensive feedstock synthesized also as a by-product or a waste in the synthesis of biodiesel from an oil and fat. Herein, "%" expressing the concentration of a component means "vol % (v/v %)" when the component is a liquid, and means "wt % (w/v %)" when the component is a solid.

With regard to an inorganic nitrogen source in the medium in the present invention, the medium needs to contain a nitrogen source that can be utilized by the $C_1$ compound-assimilating bacterium and/or the yeast of the present invention, for example, the bacterium of the genus *Methylobacterium* and/or the yeast of the genus *Rhodotorula*, and needs to contain, for example, an ammonium salt. Specific examples thereof include ammonium chloride ($NH_4Cl$) and/or ammonium dihydrogen phosphate (($NH_4$)$H_2PO_4$). With regard to the concentration of the ammonium salt contained in the medium, the ammonium salt is suitably contained at a concentration of from 0.2 g/L to 2.0 g/L.

With regard to a mineral component in the medium in the present invention, the medium needs to contain a mineral component that can be utilized by the $C_1$ compound-assimilating bacterium and/or the yeast of the present invention, for example, the bacterium of the genus *Methylobacterium* and/or the yeast of the genus *Rhodotorula*. Examples thereof include ammonium chloride and magnesium sulfate.

Examples of other components to be contained in the medium in the present invention include vitamins. Examples of the kinds of the vitamins include B vitamins, such as thiamine hydrochloride (vitamin B1), vitamin B2, pyridoxine hydrochloride (vitamin B6), vitamin B12, niacin, pantothenic acid, folic acid, p-aminobenzoic acid (folic acid precursor), biotin, and inositol.

In the present invention, the culture conditions of the $C_1$ compound-assimilating bacterium and/or the yeast for EGT production may be appropriately selected from conditions that allow the production of EGT and hardly kill the bacterium and/or the yeast. The culture may be preferably performed at about 28° C. A culture time is not particularly limited as long as the condition allows the production of EGT and hardly kills the bacterium and/or the yeast. For example, in the case where the culture is performed at 28° C. using a liquid medium containing 2 vol % methanol, when a state in which EGT is accumulated in the cells and the bacterium and/or the yeast is not killed can be maintained, the culture may be continued even under a state in which the growth of the bacterium and/or the yeast maintains an equilibrium state. Specifically, the culture time may be set to 7 days or more, and when an EGT amount in the cells continues to increase even under a state in which the growth of the bacterium and/or the yeast maintains an equilibrium state through 30-day culture, the culture may be continued. For the optimization of culture conditions, for example, production amounts may be comparatively investigated in 7-day culture.

Particularly in the case of the bacterium of the genus *Methylobacterium* out of the $C_1$ compound-assimilating bacterium of the present invention, genes involved in EGT production on the genome include egtABCDE. For example, in *M. aquaticum* strain MA-22A, egtBD are encoded tandemly, and egtA, C and E are encoded indifferent loci (see FIG. 1). The egtBD genes are genes important for EGT production. For example, in the case of an egtBD gene-deletion strain of *M. aquaticum* strain MA-22A, a cell growth rate is slightly increased as compared to the wild type, but EGT is not produced at all.

EGT accumulated in the cells by culturing the $C_1$ compound-assimilating bacterium and/or the yeast of the present invention may be extracted from the cells and purified. The extraction of EGT from the cells may be performed by, for example, a thermal extraction method. The thermal extraction may be performed by treating a suspension of the cells in water at from 60° C. to 98° C., preferably from 80° C. to 98° C., for example, about 95° C. for about 10 minutes. A method known per se or any method to be developed in the future may be applied as a method for the purification. For example, the purification may be performed by an HPLC technique.

The method of the present invention is particularly excellent in the following respect as compared to a method involving producing and purifying EGT by a related-art method. For example, in Patent Literature 1 (JP 2012-105618 A), there is a report that EGT extracted from the golden oyster mushroom (*Pleurotus cornucopiae* var. *citrinopileatus*) reaches a production amount of 450 mg/L under optimal conditions, but as described in the "Background Art" section, the culture and extraction method still has problems with cost and the like because of, for example, a long culture time of the fungus (14 days for primary culture and 14 days for secondary culture), the use of an organic solvent in the extraction of EGT from the cells of the fungus, and the supplementation of a medium with methionine. On the other hand, according to the method involving producing EGT with the $C_1$ compound-assimilating bacterium and/or the yeast of the present invention, the culture time of the bacterium and/or the yeast is short, and there is no need to use an organic solvent in the extraction of EGT from the cells. There is also no need to supplement the medium for culturing the cells with methionine.

EXAMPLES

The present invention is described below by way of Examples for further understanding of the present invention. Needless to say, however, the present invention is not limited only to the description of these Examples.

(Example 1) Production of EGT by Various Bacterial Strains

First, EGT production was confirmed for various bacterial strains of bacterium of the genus *Methylobacterium* whose genomic information was known.

(1) Bacterial Strains

EGT production capacities were confirmed for the following bacterium of the genus *Methylobacterium*: *M. oryzae* DSM18207, *M. aquaticum* strain MA-22A (international accession number: FERM BP-11078), *M. extorquens* (NRBC15687T), *M. radiotolerans* (IAM12098T), and *M. extorquens* strain AM1 (ATCC14718).

(2) Methanol/Mineral Medium

A methanol/mineral medium was formed of a mineral salt solution (200 mL), a buffer (300 mL), an iron solution (0.33 mL), a TE solution (1 mL), a vitamin solution (10 mL), methanol, and water, and was prepared by sterilizing each of the solutions, followed by mixing. The compositions of the solutions are as described below.

Mineral salt solution: 8.09 g of $NH_4Cl$ and 1.0 g of $MgSO_4.7H_2O$ per 1 L

Buffer: 8.0 g of $K_2HPO_4$ and 3.6 g of $NaH_2PO_4.H_2O$ per 1 L

Iron solution: 13.9 g of $FeSO_4.7H_2O$ per 1 L dissolved in 1 M hydrochloric acid Vitamin solution: 0.4 g of calcium pantothenate, 0.2 g of inositol, 0.4 g of niacin, 0.2 g of p-aminobenzoic acid, 0.4 g of pyridoxine hydrochloride, 0.4 g of thiamine hydrochloride, 0.2 g of biotin, and 0.2 g of vitamin B12 per 1 L Methanol was used at different concentrations.

When used, ethanol, succinate, or glucose was used at a predetermined concentration in place of methanol.

(3) Culture of Various Bacterial Strains

Among various bacterial strains, bacterium of the genus *Methylobacterium* were cultured for 7 days using the methanol/mineral medium containing 3 vol % methanol. *M. aquaticum* strain MA-22A was cultured at 28° C. for 7 days using the methanol/mineral medium containing 0.5 vol % methanol.

(4) Confirmation of EGT Production Capacity

The various bacteria cultured in the liquid medium were centrifuged at 25° C. and 12,000×g for 10 minutes, and the resultant bacterial cells were washed with 0.85 wt % NaCl. The wet weight of the bacteria was measured and recorded. 1 mL of water was added per 10 mg to 50 mg of the wet weight of the bacteria, followed by treatment at 95° C. for 10 minutes to extract EGT in the bacterial cells. A suspension of the cells was treated at 1,600 rpm for 30 minutes using a mixer (Vortex), and then centrifuged at 25° C. and 14,000×g for 10 minutes to provide a supernatant. Cell debris was removed. The resultant supernatant was subjected to membrane filtration through a 0.2 μm filter, and an EGT production amount was measured for the filtrate.

In this Example, the EGT amount was quantified by HPLC using an Asahipak $NH_2P$-50 column. EGT was eluted using a concentration gradient liquid formed of eluent A (0.1 vol % triethylamine, 50 mM sodium phosphate buffer: pH 7.3) and eluent B (100 mM NaCl). The EGT amount was measured on the basis of an absorbance at a wavelength of 254 nm. Under such measurement conditions, the elution of EGT was observed at about 6.1 min.

Figure 2:
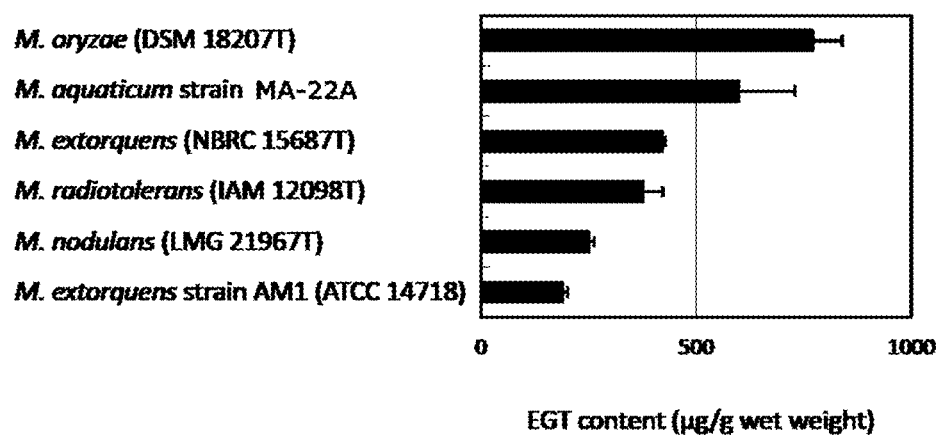
FIG. 2 is a graph for showing the results of quantification of EGT production for various bacterial strains of bacterium of the genus *Methylobacterium* by HPLC analysis (wavelength: 254 nm) (Example 1).

The EGT production amounts in the various bacterial strains described above are shown in FIG. 2. As a result of the culture of the various bacterial strains in the methanol/mineral medium for 7 days, it was confirmed that EGT was produced with wet weight values of from about 200 μg/g to about 800 μg/g. *M. oryzae* DSM18207 had the highest EGT production amount, and *M. aquaticum* strain MA-22A had the second highest value.

(Example 2) EGT Production Amount Depending on Difference Among Various Carbon Sources EGT production capacity was confirmed for *M. aquaticum* strain MA-22A in the case where a carbon source in a medium and its concentration were changed.

Culture was performed at 28° C. for 7 days using 5 mL of any one of: the methanol/mineral medium described in Example 1 containing methanol (0.5 vol %, 1 vol %, 2 vol %, or 3 vol %), or an alternative carbon source to methanol, specifically any one of ethanol (0.5 vol %, 1 vol %, or 1.5 vol %), succinate (1 wt %, 2 wt %, or 3 wt %), and glucose (0 wt %, 1 wt %, 2 wt %, or 3 wt %); Luria-Bertani medium (LB medium) containing methanol (0 vol %, 1 vol %, 2 vol %, or 3 vol %) as a carbon source (LB+Methanol); and Middlebrook $7H_9$ medium for the bacterium of the genus *Mycobacterium*, a mineral medium containing sodium citrate and glutamate as carbon sources, supplemented with methanol (0 vol %, 1 vol %, 2 vol %, or 3 vol %) (7H9+Methanol).

Figure 3:
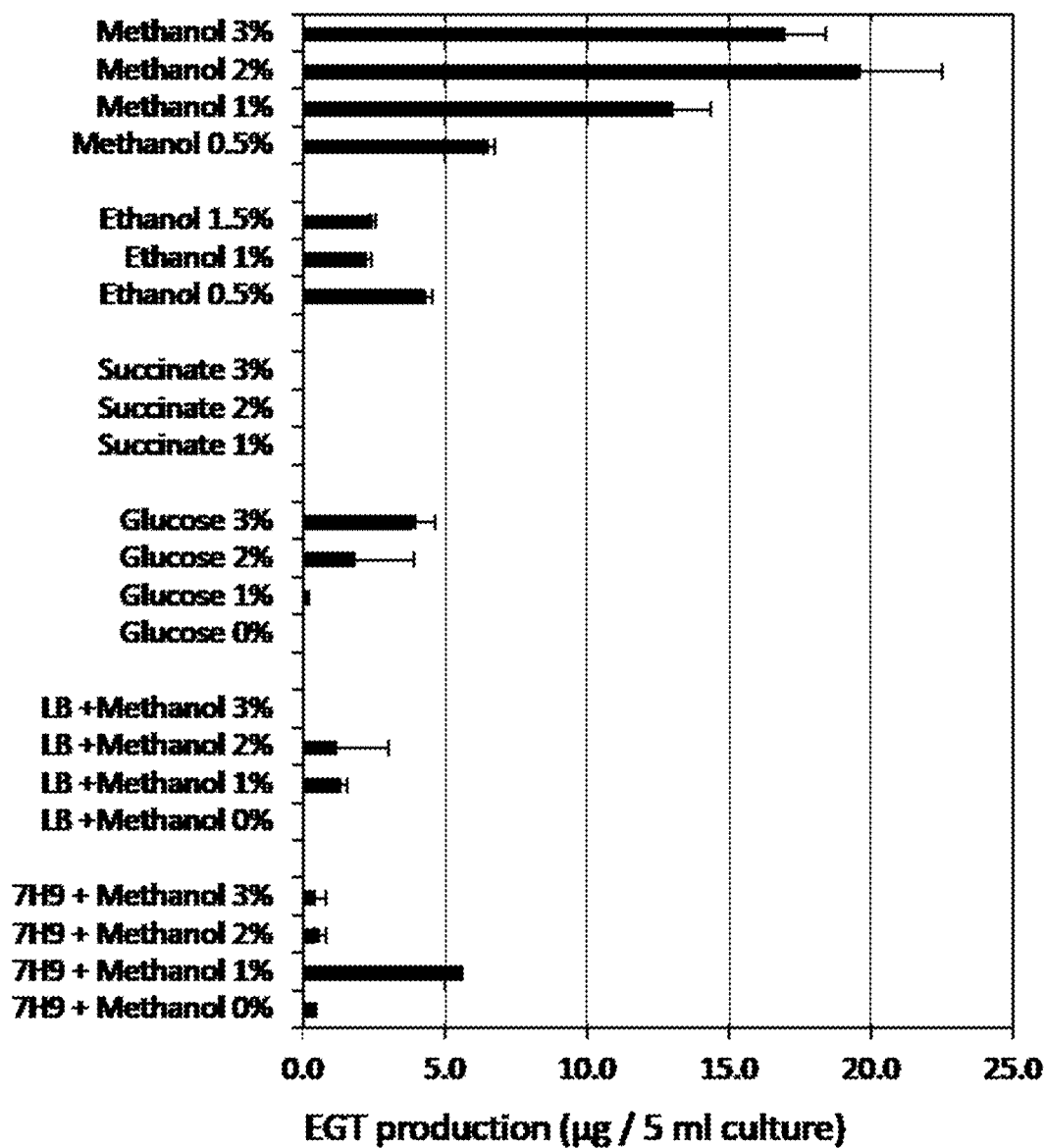
FIG. 3 is a graph for showing the results of quantification of EGT production by *M. aquaticum* strain MA-22A in the case where a carbon source in a methanol/mineral medium is changed (Example 2).

An EGT production amount was quantified by HPLC in accordance with the method described in Example 1. As a result of the difference among the carbon sources, a difference in EGT production amount was found (FIG. 3). The EGT production amount per wet weight was highest when the carbon source was methanol.

(Example 3) EGT Production Amount and Bacterial Growth in the Case where Methanol Concentration is Changed EGT production capacity was confirmed for *M. aquaticum* strain MA-22A in the case where a methanol concentration in a medium was changed. Culture was performed at 28° C. for 38 days using 100 mL of the methanol/mineral medium described in Example 1 containing methanol at any of various concentrations (0.5 vol %, 1 vol %, 2 vol %, or 3 vol %). An EGT production amount was quantified by HPLC in accordance with the method described in Example 1.

Figure 4:
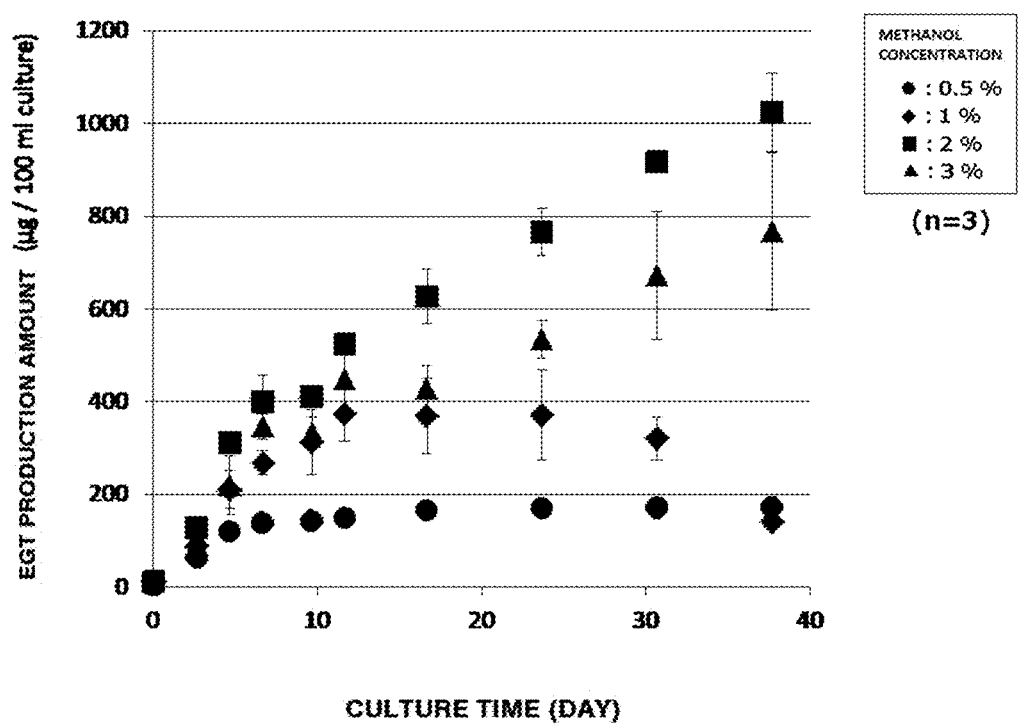
FIG. 4 is a graph for showing the results of quantification of EGT production by *M. aquaticum* strain MA-22A in the case where the supplementation concentration of methanol in the methanol/mineral medium is changed (Example 3).

As a result of the difference in methanol concentration, a difference in EGT production amount was found (FIG. 4). The EGT production amount per wet weight was highest when the methanol concentration in the medium was 2 vol %, and it was found that EGT was accumulated in bacterial cells by continuing the culture. Meanwhile, the accumulation amount of EGT and the bacterial growth did not coincide with each other. The culture reached a stationary phase in from 3 days to 7 days irrespective of the methanol concentration, and the turbidity of the culture broth did not increase thereafter. However, the EGT accumulation amount per bacterial cell continued to increase particularly when the methanol concentration was 2 vol % or 3 vol %. In this experiment, a maximum productivity of 1 mg/100 mL culture broth (1.2 mg/g wet weight cells, 6.3 mg/g dry weight cells) was exhibited when 2 vol % methanol was used.

(Example 4) EGT Production Amount in the Case where Kind of Nitrogen Source is Changed EGT production capacity was confirmed for *M. aquaticum* strain MA-22A in the case where a nitrogen source in a medium was changed.

Figure 5:
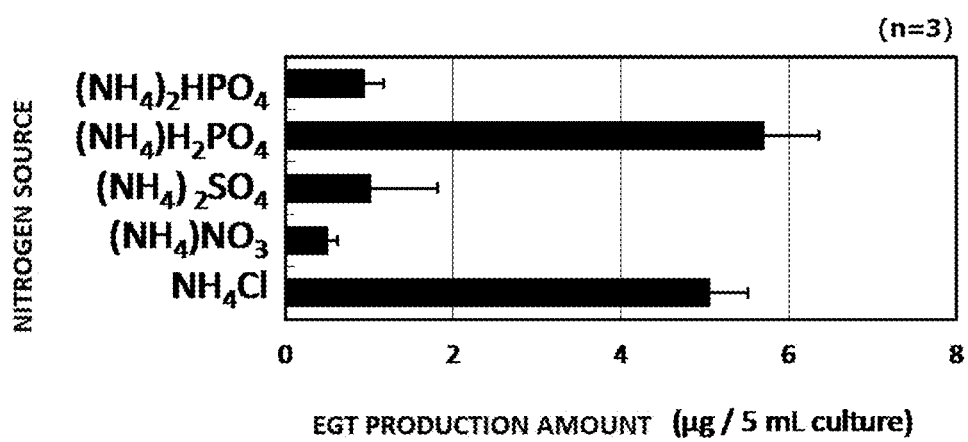
FIG. 5 is a graph for showing the results of quantification of EGT production by *M. aquaticum* strain MA-22A in the case where a nitrogen source in the methanol/mineral medium is changed (Example 4).

Culture was performed under the following condition: $NH_4Cl$ contained as the nitrogen source of the methanol/mineral medium described in Example 1 was changed to another nitrogen compound. The culture was performed at 28° C. for 7 days using 5 mL of a medium containing 0.4 g/L of any one of $NH_4Cl$, $(NH_4)_2HPO_4$, $(NH_4)H_2PO_4$, $(NH_4)_2SO_4$, and $(NH_4)NO_3$. An EGT production amount was quantified by HPLC in accordance with the method described in Example 1. A high EGT production amount was found when $(NH_4)H_2PO_4$ or $NH_4Cl$ was used as the nitrogen source (FIG. 5).

Figure 6:
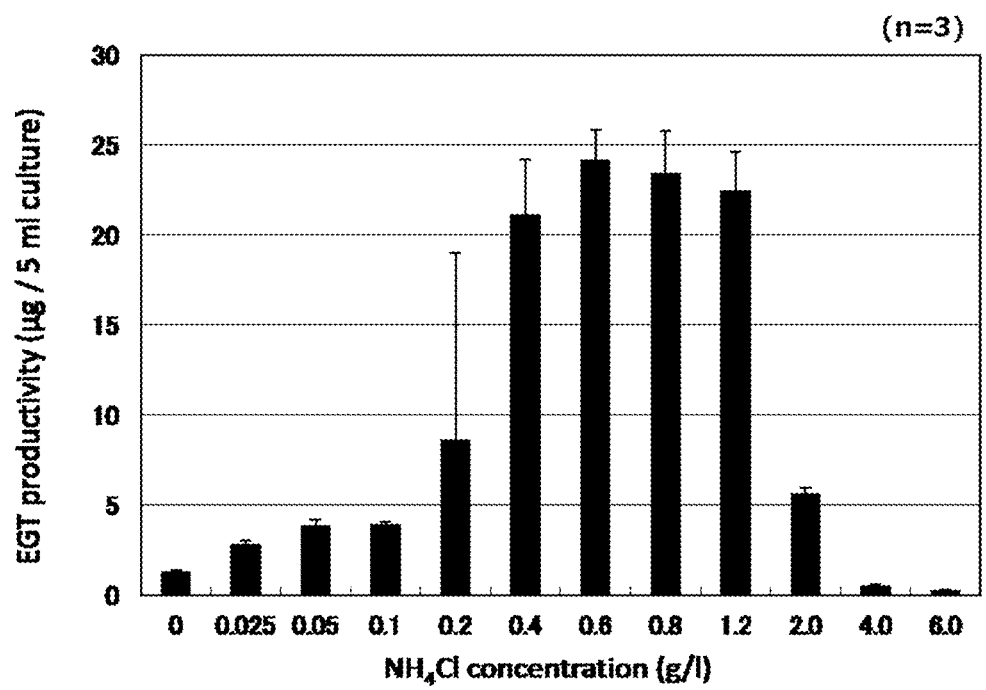
FIG. 6 is a graph for showing the results of quantification of EGT production by *M. aquaticum* strain MA-22A in the case where a nitrogen source concentration in the methanol/mineral medium is changed (Example 5).

(Example 5) EGT Production Amount in the Case where $NH_4Cl$ Concentration is Changed EGT production capacity was confirmed for *M. aquaticum* strain MA-22A in the case where an $NH_4Cl$ concentration in a medium was changed. Culture was performed at 28° C. for 7 days using 5 mL of the methanol/mineral medium described in Example 1 containing $NH_4Cl$ at any of various concentrations (0.025 g/L, 0.05 g/L, 0.1 g/L, 0.2 g/L, 0.4 g/L, 0.6 g/L, 0.8 g/L, 1.2 g/L, 2.0 g/L, 4.0 g/L, or 6.0 g/L). An EGT production amount was quantified by HPLC in accordance with the method described in Example 1. As a result of the difference in $NH_4Cl$ concentration in the medium, a difference in EGT production amount was found, and the production amount per 5 mL of the medium was highest in the case of from 0.4 g/L to 1.2 g/L (FIG. 6).

Figure 7:
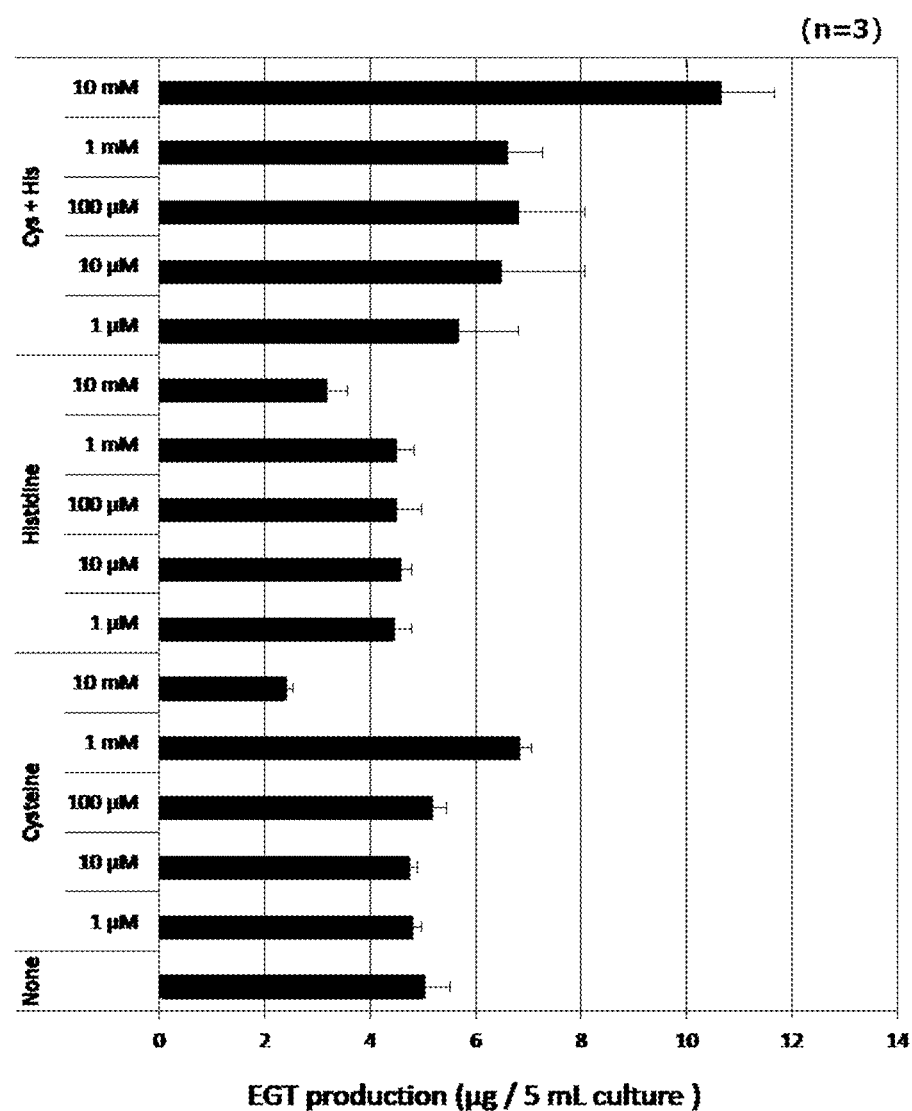
FIG. 7 is a graph for showing the results of quantification of EGT production by *M. aquaticum* strain MA-22A in the case where an amino acid for supplementing the methanol/mineral medium is changed (Example 6).

(Example 6) EGT Production Amount in the Case where Medium is Supplemented with Amino Acid EGT production capacity was confirmed for *M. aquaticum* strain MA-22A in the case where a medium was supplemented with an amino acid at various concentrations. Culture was performed at 28° C. for 7 days using 5 mL of the methanol/mineral medium described in Example 1 containing histidine (His) and/or cysteine (Cys) at any of various concentrations. An EGT production amount was quantified by HPLC in accordance with the method described in Example 1. Histidine and cysteine are precursors of EGT. The production amount per 5 mL of the medium was highest when histidine and cysteine were each contained at 10 mM (FIG. 7).

Figure 8:
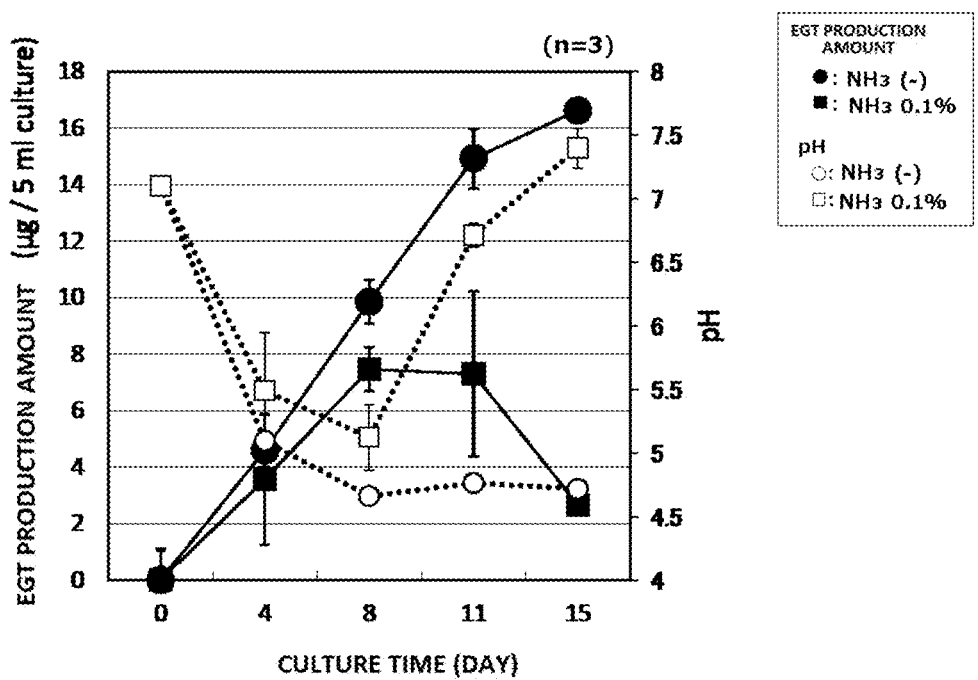
FIG. 8 is a graph for showing the results of confirmation of changes in EGT production capacity and pH in *M. aquaticum* strain MA-22A depending on the presence or absence of $NH_3$ to be added to the methanol/mineral medium (Example 7).

(Example 7) EGT Production Amount Depending on Presence or Absence of Nitrogen Source For *M. aquaticum* strain MA-22A, it was conceivable that, when methanol serving as the carbon source and ammonium chloride serving as the nitrogen source were consumed during culture, further growth was not expected and the pH of the medium was reduced to inhibit growth. Therefore, an investigation was performed by adding ammonia and methanol on day 4, day 8, and day 11 of culture. *M. aquaticum* strain MA-22A was cultured in 100 mL of the methanol/mineral medium described in Example 1, 1 mL of a 10 vol % aqueous solution of ammonium hydroxide (final concentration: 0.1 vol % in terms of nitrogen source) and 2 mL of methanol (final concentration: 2 vol %) were added, and an EGT amount and the pH of the medium were measured. The culture was performed at 28° C. for 15 days. The EGT production amount was quantified by HPLC in accordance with the method described in Example 1. When the addition was performed, the pH was able to be maintained near neutral, but the EGT production amount peaked on day 8 to day 11 of culture and showed a tendency to reduce thereafter. On the other hand, when the addition was not performed, the pH reduced to 5 or less, but the EGT production amount continued to increase even at a culture time of 15 days (FIG. 8).

(Example 8) Genes Involved in EGT Production

Figure 9:
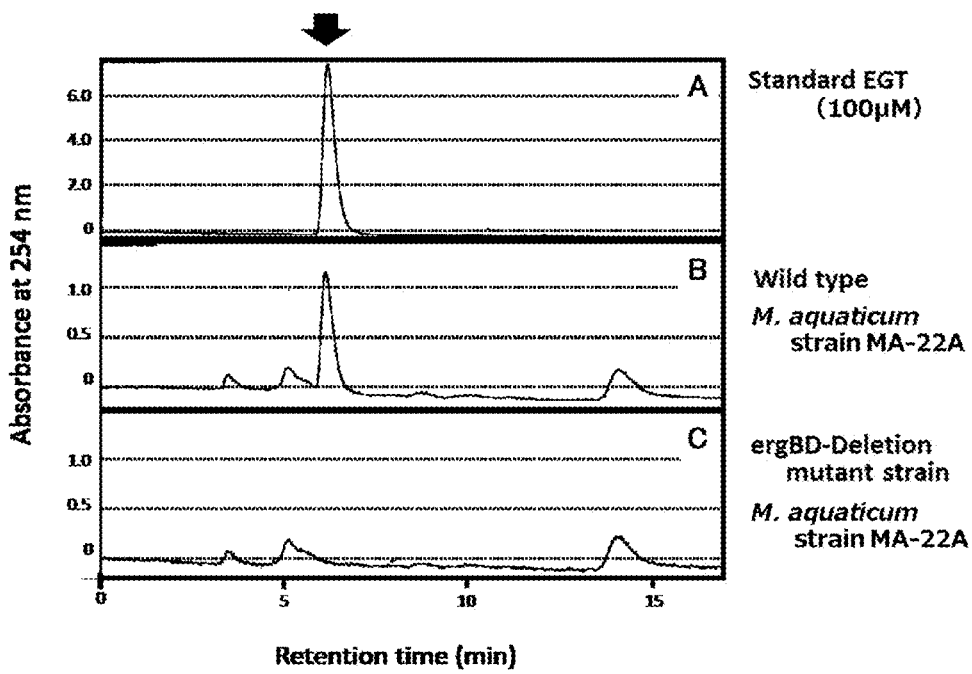
FIG. 9 are charts for showing the results of analysis of EGT production capacity in an ergBD-deletion mutant strain (AergBD) by HPLC (Example 8).

Genes homologous to egtABCDE genes in *Mycobacterium* were searched for in the genome of *M. aquaticum* strain MA-22A by BLAST analysis. It was confirmed that, in *M. aquaticum* strain MA-22A, egtBD (contig 199) were encoded tandemly, and egtA, C and E were encoded in different loci (FIG. 1). In order to elucidate the function of EGT in *M. aquaticum* strain MA-22A, an ergBD-deletion mutant strain (AergBD) was constructed by homologous recombination. The EGT production capacity of AergBD was quantified by HPLC after the extraction treatment of EGT in accordance with the method described in Example 1. The results are shown in FIG. 9. In HPLC analysis by absorbance measurement at a wavelength of 254 nm, EGT was detected at 6.2 minutes for each of standard EGT (100 μM) and the extract of wild-type *M. aquaticum* strain MA-22A, but EGT was not observed for the extract of AergBD. This suggested that the egtBD genes were genes required in EGT production.

Figure 10:
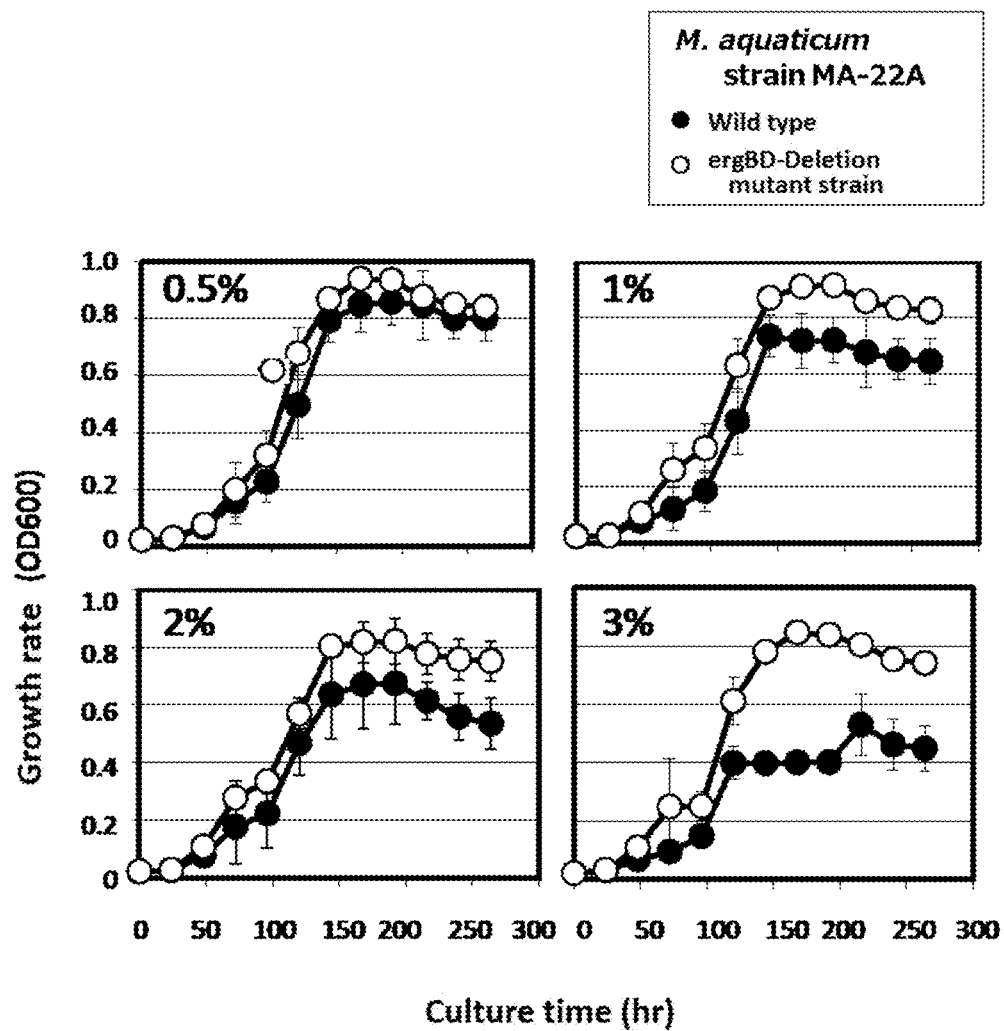
FIG. 10 are graphs for showing the results of confirmation of bacterial growth in the case where a methanol concentration in a medium is changed for each of *M. aquaticum* strain MA-22A wild type and AergBD (Example 9).

(Example 9) Bacterial Growth in the Case where Methanol Concentration is Changed Bacterial growth was confirmed for each of *M. aquaticum* strain MA-22A wild type and AergBD in the case where a methanol concentration in a medium was changed. Each bacterial strain was cultured in a 96-well plate at 28° C. for 300 hours using 200 μL of the methanol/mineral medium described in Example 1 containing methanol at any of various concentrations (0.5 vol %, 1 vol %, 2 vol %, or 3 vol %). A bacterial cell yield was quantified by absorbance (OD600) measurement at a wavelength of 600 nm. As a result, AergBD showed more satisfactory growth in the medium containing 1 vol % to 3 vol % methanol than the wild strain (FIG. 10).

(Example 10) Analysis of Amino Acid Contents in Cells

Figure 11:
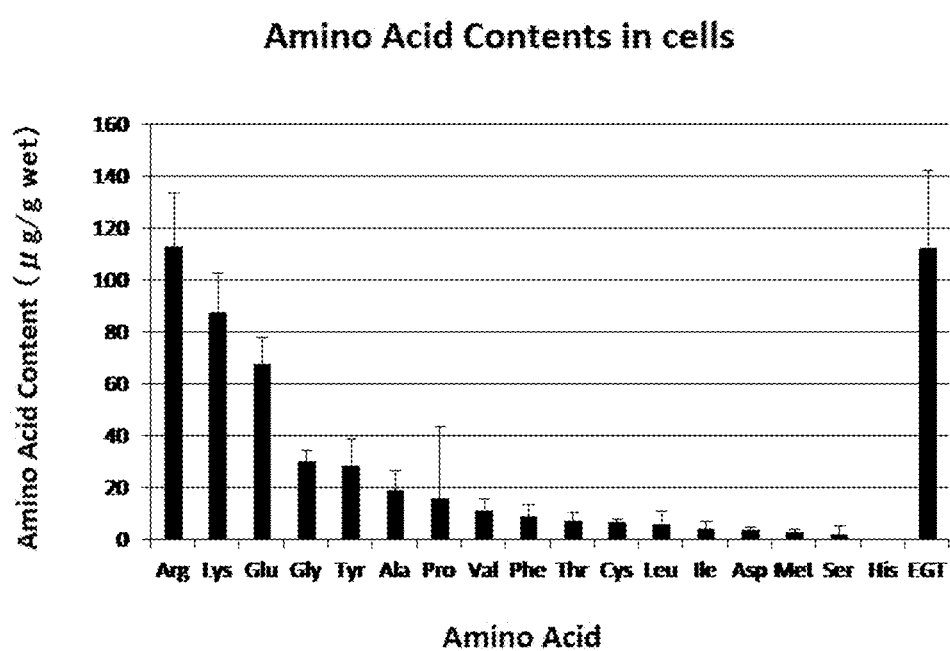
FIG. 11 is a graph for showing the results of analysis of amino acid contents in *M. aquaticum* strain MA-22A cells (Example 10).

*M. aquaticum* strain MA-22A was cultured for 7 days in the same manner as in Example 1 using 100 mL of the methanol/mineral medium containing 0.5 vol % methanol. For 10 mL of the culture broth, an EGT production amount was quantified by HPLC in accordance with the method described in Example 1. The remainder of the culture broth was used for the measurement of amino acid contents in the cells. The bacterial cells were extracted with methanol, and the extract was purified using Amberlite™ CR1310NA (4 mL resin) and then dried and redissolved in water. The resultant sample was analyzed for the amino acid contents using a high-speed amino acid analyzer (Hitachi L-8500B). As a result, it was confirmed that an EGT amount in the *M. aquaticum* strain MA-22A cells was nearly equal to an arginine amount therein (FIG. 11).

(Example 11) EGT Production by Mass Culture

*M. aquaticum* strain MA-22A was precultured for 7 days in the same manner as in Example 1 using 200 mL of the methanol/mineral medium containing 0.5 vol % methanol, and then cultured at 28° C. for 66 days using 10 L of the methanol/mineral medium containing 2 vol % methanol.

Figure 12:
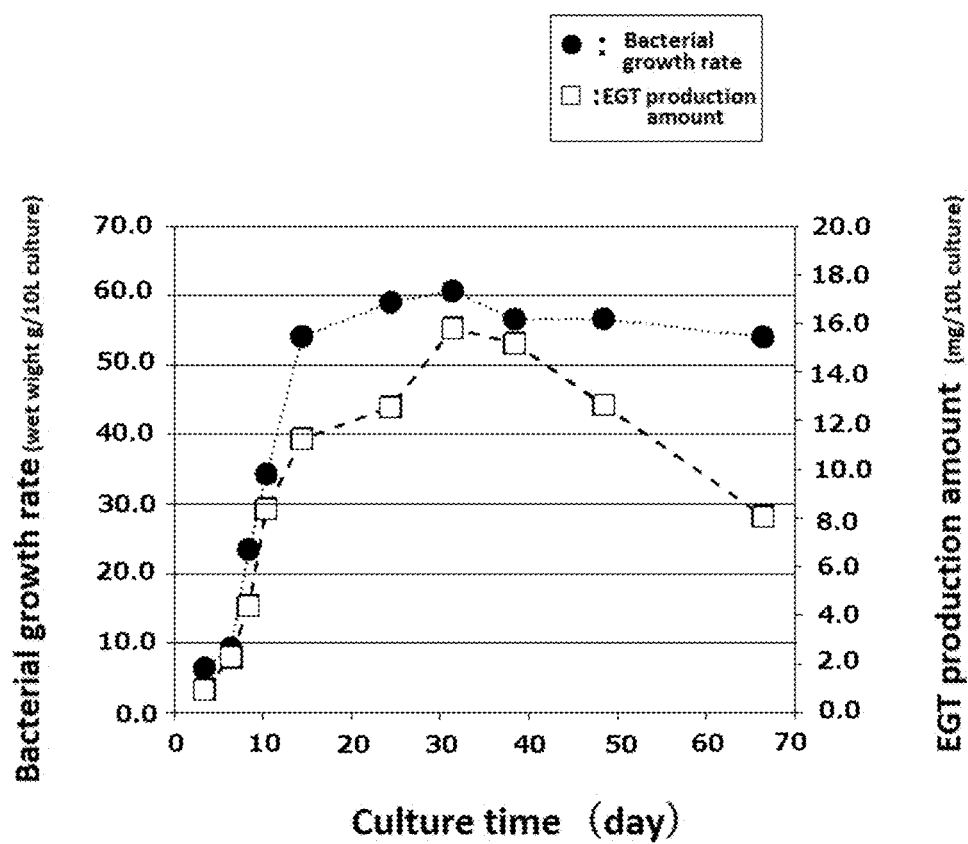
FIG. 12 is a graph for showing bacterial growth and an EGT production amount in the case where *M. aquaticum* strain MA-22A is mass-cultured (Example 11).

The culture was performed at an airflow rate of 440 mL/min under stirring at 100 rpm. The pH was not adjusted. 20 mL or 50 mL of the culture broth was occasionally taken to quantify the wet weight of the bacteria and an EGT production amount. The EGT production amount reached a peak of 15.8 mg/10 L on day 31 of culture. The EGT production amount reduced gradually, but the bacterial cell yield did not reduce very much. The productivity was low as compared to the result of Example 3, and was possibly influenced by, for example, stirring of air in a culture vessel due to scale-up (FIG. 12). However, the improvement of culture conditions can be expected to increase the EGT production amount in mass culture.

(Example 12) Influence of Methionine Supplementation on EGT Production

*M. aquaticum* strain MA-22A was cultured at 28° C. for 7 days in the same manner as in Example 1 using 5 mL of the methanol/mineral medium containing 2 vol % methanol and 0, 10 µM, 100 µM, or 1 mM methionine, and an EGT production amount was quantified by HPLC in accordance with the method described in Example 1.

Figure 13:
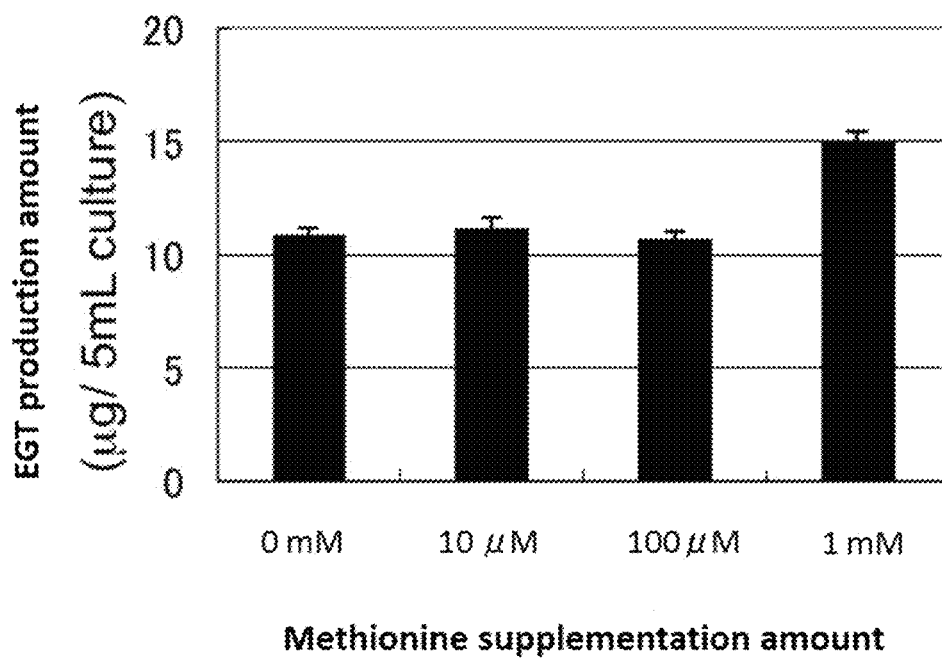
FIG. 13 is a graph for showing the results of quantification of EGT production by *M. aquaticum* strain MA-22A in the case where the methanol/mineral medium is supplemented with methionine (Example 12).

As a result, the supplementation with 1 mM methionine was found to increase the EGT production amount (FIG. 13). In the present invention, although EGT can be produced even when the medium is not supplemented with methionine, it was found that the supplementation with methionine at a suitable concentration allowed more satisfactory production of EGT.

(Example 13) Amino Acid Composition and Protein Concentration and Composition of Thermal Extract from Bacterial Cells The amino acid contents described in Example 10 were determined by extracting the amino acids in the bacterial cells with methanol. In this Example, an EGT-containing solution obtained from cultured bacterial cells by the thermal extraction described in Example 1 was investigated for its amino acid composition. The cultured bacteria, the medium, and the culture conditions are the same as those in Example 10. The thermal extraction is considered to be suited for actual EGT purification from bacterial cells. The analysis method for the amino acid composition is the same as that in Example 10.

Figure 14:
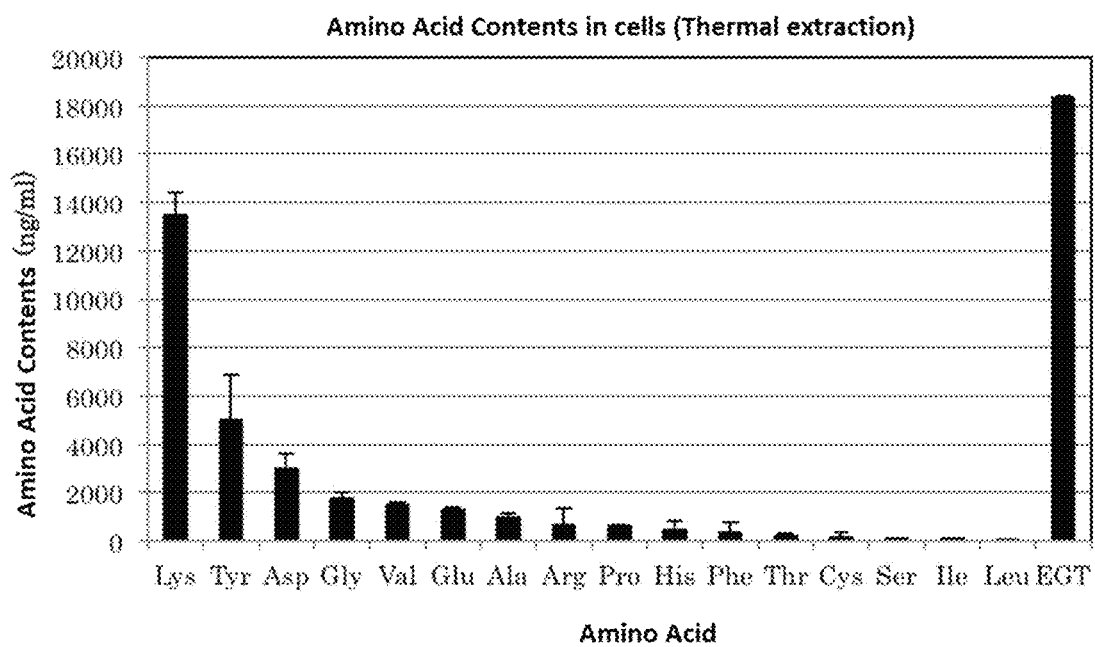
FIG. 14 is a graph for showing the results of analysis of the amounts of EGT and other amino acids for an extract solution obtained by culturing *M. aquaticum* strain MA-22A and extracting EGT from bacterial cells through heat treatment (Example 13).
Figure 15:
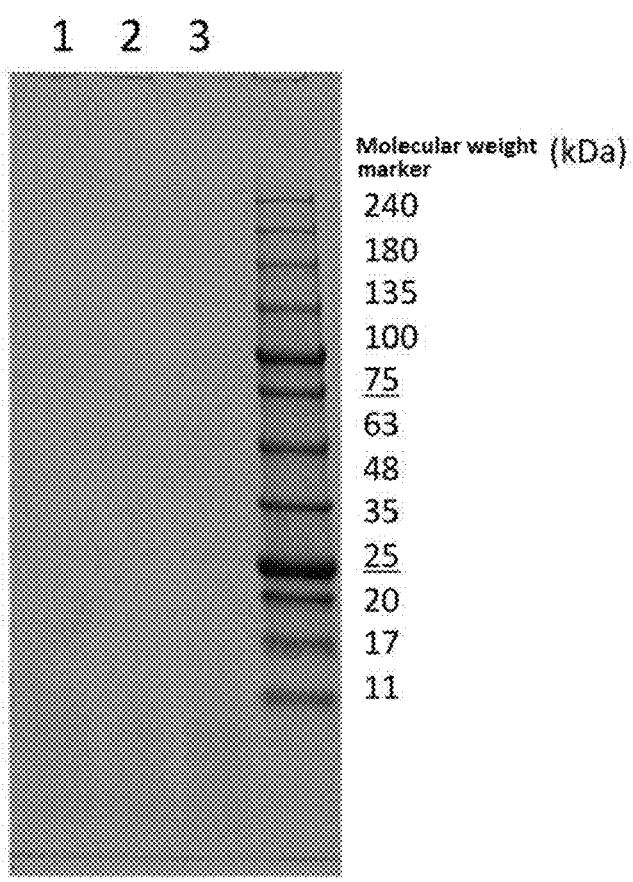
FIG. 15 is an image for showing electrophoresis results obtained by SDS-PAGE analysis of proteins for an extract solution obtained by culturing *M. aquaticum* strain MA-22A and extracting EGT from bacterial cells through heat treatment (Example 13).

The results revealed that the bacterial cells contained general amino acids in addition to EGT, and although the composition was slightly different from that obtained by extraction with methanol, EGT was most abundant in both cases (FIG. 14). In addition, it was considered that not only amino acids, but also proteins were extracted from the bacterial cells through the thermal extraction by the above-mentioned method. Therefore, the proteins were analyzed by an SDS-PAGE method. As a result, it was found that the sample contained about 0.28 mg/ml of proteins (according to a Bradford method using bovine serum albumin as a standard), and many of the contained proteins had small molecular weights of 10 kDa or less (FIG. 15).

(Example 14) EGT Production Using Glycerol as Carbon Source

In consideration of actual EGT production, glycerol was used as a carbon source other than methanol. *M. aquaticum* strain MA-22A was cultured and subjected to EGT extraction in the same manner as in the method described in Example 1 except that methanol was changed to 0.5 vol %, 1 vol %, or 2 vol % glycerol.

Figure 16:
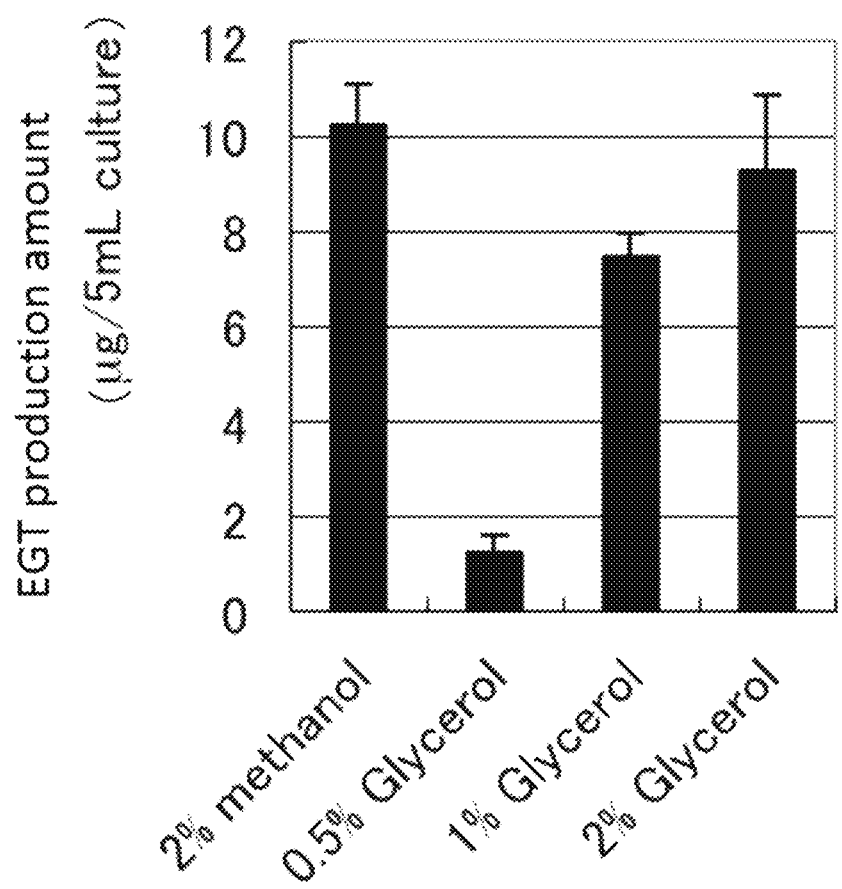
FIG. 16 is a graph for showing the results of confirmation of the EGT production capacity of *M. aquaticum* strain MA-22A in the case where culture is performed in a medium supplemented with methanol or glycerol (Example 14).

As a result, when 2 vol % glycerol was used, productivity nearly equal to the productivity in the case of using methanol was exhibited (FIG. 16).

(Example 15) EGT Production Using Methanol or Glycerol as Carbon Source

A library of the bacterium of the genus *Methylobacterium* isolated from nature (PLoS ONE 7(7): e40784. doi: 10.1371/journal.pone.0040784 (2012)) was used, and cultured and subjected to EGT extraction by the method described in Example 1 using 2 vol % methanol or 2 vol % glycerol as the carbon source.

Figure 17:
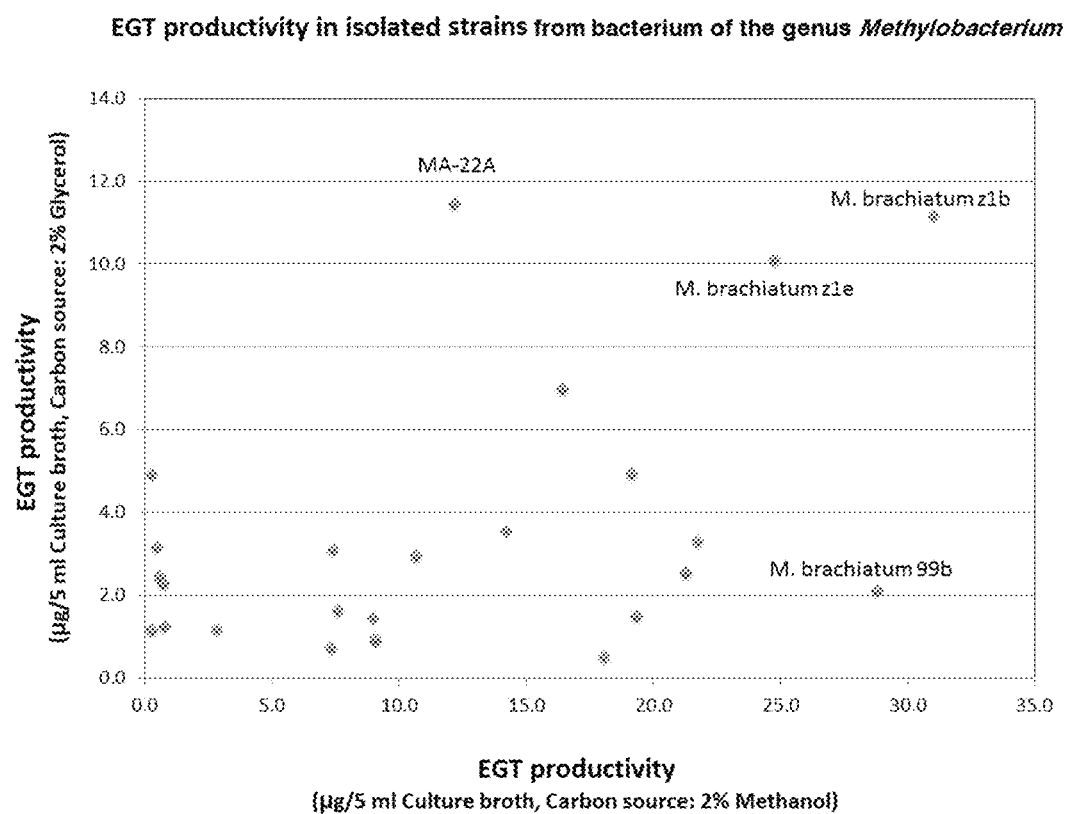
FIG. 17 is a graph for showing the results of confirmation of the EGT production capacities of various bacterium of the genus *Methylobacterium* collected from various plants in the case where the bacteria are cultured in a medium supplemented with methanol or glycerol (Example 15).
Figure 18:
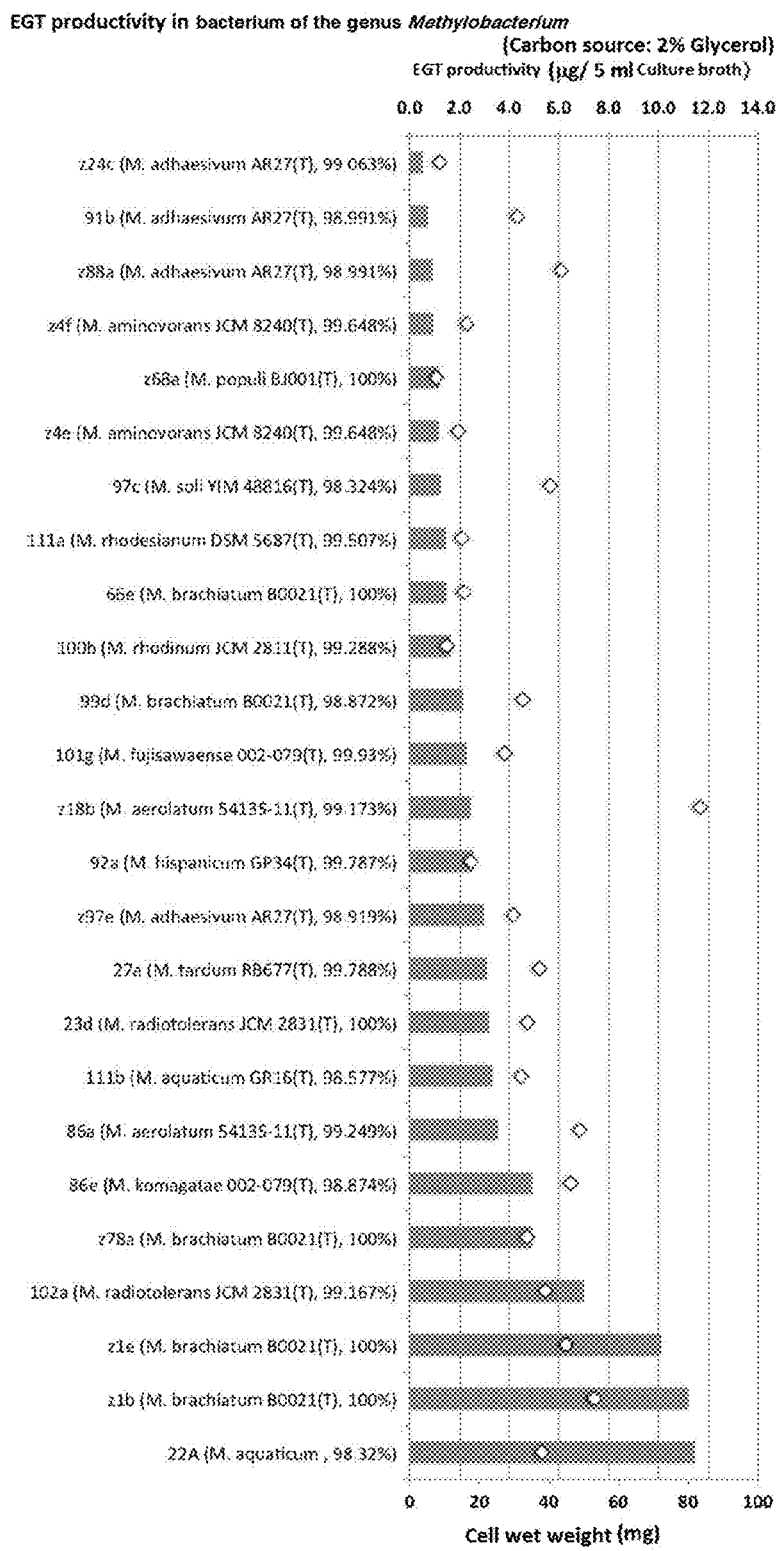
FIG. 18 is a graph for showing the results of confirmation of the EGT production capacities of various bacterium of the genus *Methylobacterium* in the case where culture is performed in a medium supplemented with glycerol (Example 15).
Figure 19:
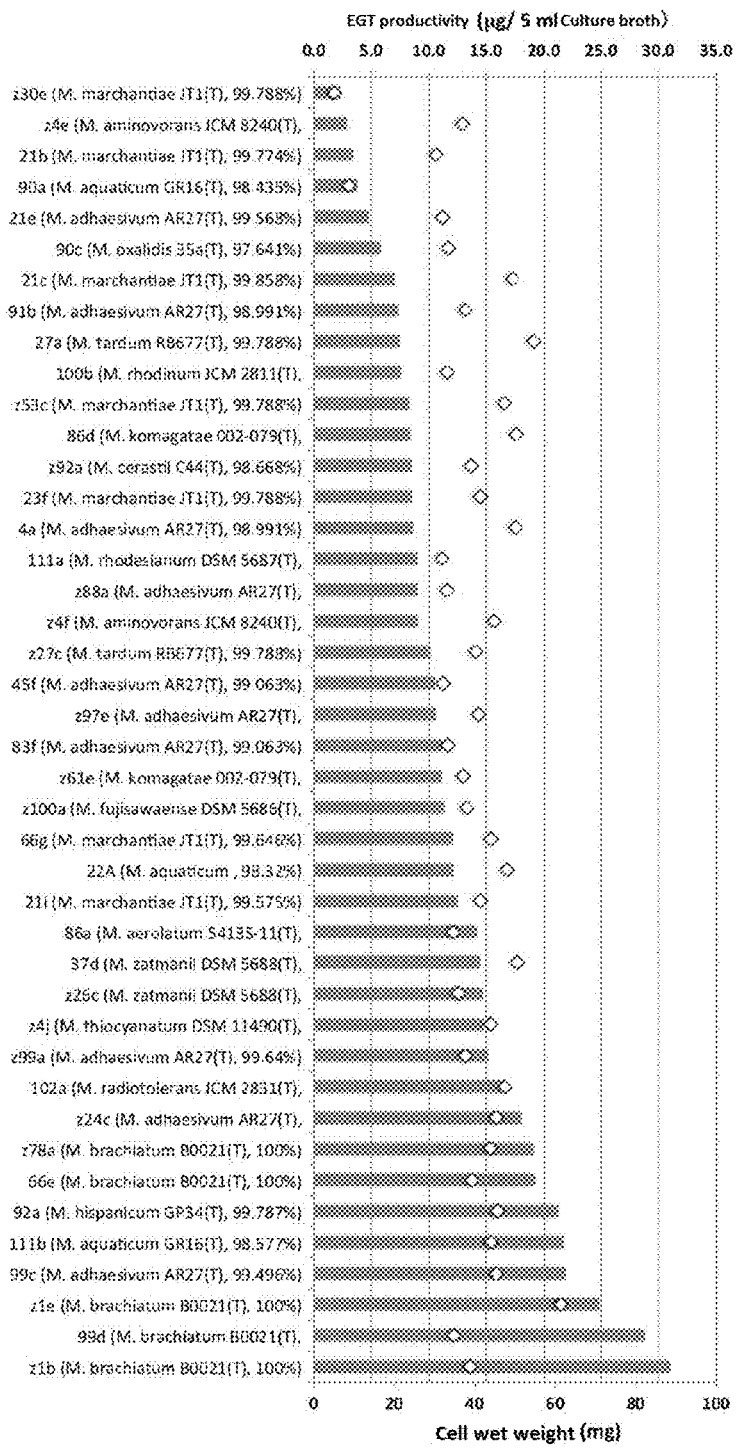
FIG. 19 is a graph for showing the results of confirmation of the EGT production capacities of various bacterium of the genus *Methylobacterium* in the case where culture is performed in a medium supplemented with methanol (Example 15).

As a result, *M. aquaticum* strain MA-22A did not show a change in EGT productivity irrespective of which carbon source was used, as in the results described in Example 14 (FIG. 17). Bacterial strains having higher productivity than *M. aquaticum* strain MA-22A in the case of using methanol were found, but did not have productivity as high as that of *M. aquaticum* strain MA-22A in the case of using glycerol (FIG. 18 and FIG. 19). In FIG. 18 and FIG. 19, bar graphs represent EGT productivity, and rhombuses represent cell wet weight. Of the library of the bacterium of the genus *Methylobacterium*, *M. brachiatum* strain 99d, *M. brachiatum* strain zlb, and *M. brachiatum* strain zle were domestically deposited to NITE Patent Microorganisms Depositary (room 112, 2-5-8 Kazusakamatari, Kisarazu-shi, Chiba) under the accession numbers NITE P-02088, NITE P-02089, and NITE P-02090 (domestic accession date: Jul. 15, 2015), followed by conversion to an international deposit under the Budapest Treaty (accession numbers: NITE BP-02088, NITE BP-02089, and NITE BP-02090).

(Example 16) EGT Production by Yeasts

EGT production capacities were confirmed for the following yeasts isolated from nature: *Rhodotorula mucilaginosa* z41c, *Rhodotorula mucilaginosa* z41d, and *Cryptococcus flavescens* z64b (PLoS ONE 7 (7):e40784.doi: 10.1371/journal.pone.0040784 (2012)). Those yeasts were cultured and subjected to EGT extraction by the method described in Example 1 using 2% methanol or 2% glycerol as the carbon source.

Figure 20:
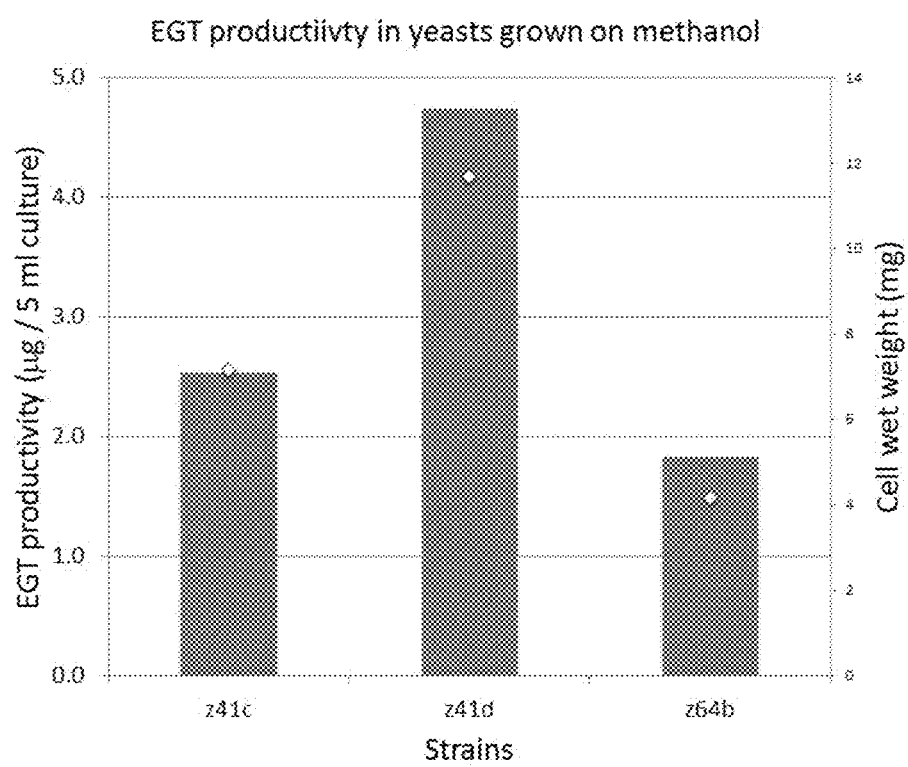
FIG. 20 is a graph for showing the results of confirmation of the EGT production capacities of yeasts in the case where culture is performed in a medium supplemented with methanol (Example 16).
Figure 21:
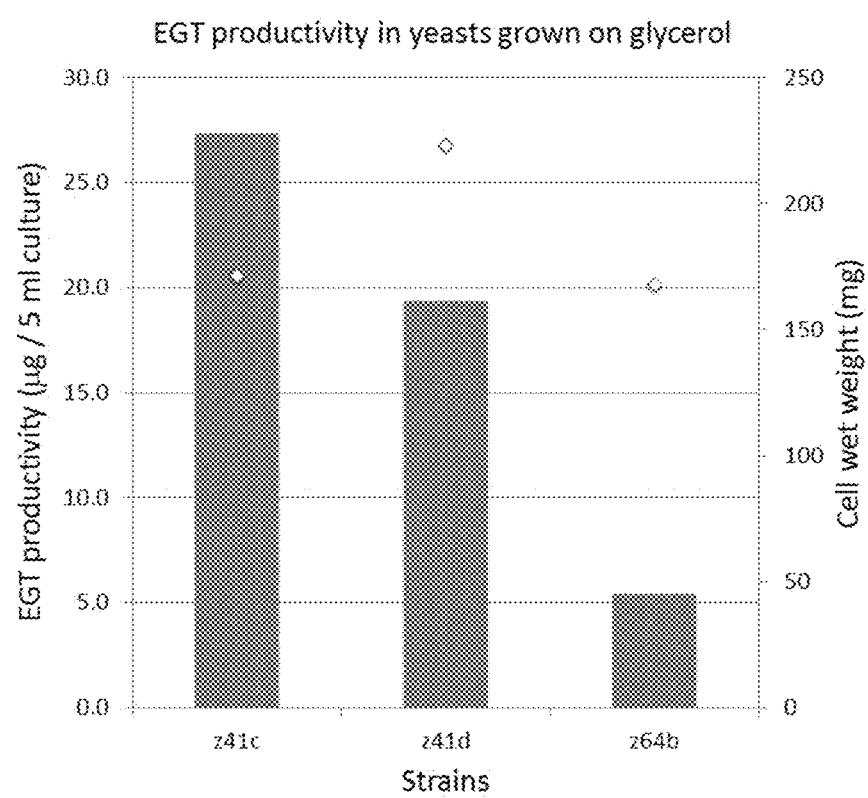
FIG. 21 is a graph for showing the results of confirmation of the EGT production capacities of yeasts in the case where culture is performed in a medium supplemented with glycerol (Example 16).

The results are shown in FIG. 20 and FIG. 21. In FIG. 20 and FIG. 21, bar graphs represent EGT productivity, and rhombuses represent cell wet weight. As shown in FIG. 20, through the culture in the medium containing methanol, EGT productivity was found in each of the *Rhodotorula mucilaginosa* z41c, *Rhodotorula mucilaginosa* z41d, and *Cryptococcus flavescens* z64b strains. In addition, it was confirmed that each of *Rhodotorula mucilaginosa* z41c, *Rhodotorula mucilaginosa* z41d, and *Cryptococcus flavescens* z64b had higher EGT productivity in the case of using the medium containing glycerol than in the case of using the medium comprises methanol.

*Rhodotorula mucilaginosa* z41c and *Rhodotorula mucilaginosa* z41d were internationally deposited to NITE Patent Microorganisms Depositary (room 112, 2-5-8 Kazusakamatari, Kisarazu-shi, Chiba) under the accession numbers NITE BP-02171 and NITE BP-02172 (date of acceptance: Dec. 4, 2015).

INDUSTRIAL APPLICABILITY

As described in detail above, according to the method of producing EGT with the $C_1$ compound-assimilating bacte-

The invention claimed is:

1. A manufacturing method for ergothioneine, comprising the steps of:
   culturing an ergothioneine-producing bacterium of *Methylobacterium aquaticum* and/or a budding yeast selected from *Rhodotorula mucilaginosa* and *Cryptococcus flavescens* in a medium comprising a carbon source to produce ergothioneine; and
   collecting the produced ergothioneine from the resulting culture.

2. The manufacturing method for ergothioneine according to claim 1, wherein said medium comprising methanol, methylamine, and/or glycerol as the carbon source, to produce ergothioneine.

3. The manufacturing method according to claim 1, wherein the budding yeast is *Cryptococcus flavescens*.

4. The manufacturing method according to claim 1, wherein the medium comprises the carbon source with a concentration of from 0.1% to 5%.

5. The manufacturing method according to claim 1, wherein the medium further comprises an ammonium salt at with a concentration of from 0.2 g/L to 2.0 g/L.

6. The manufacturing method according to claim 1, wherein the medium comprises ammonium chloride or ammonium dihydrogen phosphate as an ammonium salt.

7. A manufacturing method for ergothioneine, comprising the the steps of:
   culturing an ergothioneine-producing bacterium of *Methylobacterium aquaticum* and/or a budding yeast selected from *Rhodotorula mucilaginosa* and *Cryptococcus flavescens* in a medium comprising a carbon source, to produce ergothioneine; and
   subjecting the cultured bacterium and/or budding yeast to heat treatment to extract the produced ergothioneine therefrom; and
   collecting the extracted ergothioneine from the resultant.

8. The manufacturing method for ergothioneine according to claim 1, wherein the bacterium is a bacterium selected from those of the *Methylobacterium aquaticum* respectively deposited under the accession numbers NITE BP-02088, NITE BP-02089, and NITE BP-02090.

9. The manufacturing method for ergothioneine according to claim 1, wherein the budding yeast is a yeast selected from budding yeasts of the *Rhodotorula mucilaginosa* respectively deposited under the accession numbers NITE BP-02171 and NITE BP-02172.

10. The manufacturing method according to claim 1, wherein the budding yeast is an imperfect yeast.

11. The manufacturing method according to claim 7, wherein the medium further comprises an ammonium salt with a concentration of from 0.2 g/L to 2.0 g/L.

12. The manufacturing method according to claim 7, wherein the medium comprises ammonium chloride or ammonium dihydrogen phosphate as an ammonium salt.

13. The manufacturing method according to claim 7, wherein the medium comprises the carbon source with a concentration of from 0.1% to 5%.

14. A manufacturing method for ergothioneine, comprising the steps of:
   culturing an ergothioneine-producing bacterium selected from those of the *Methylobacterium aquaticum* respectively deposited under the accession numbers NITE BP-02088, NITE BP-02089, and NITE BP-02090 or a yeast selected from budding yeast of the *Rhodotorula mucilaginosa*, respectively deposited with under the accession numbers NITE BP-02171 and NITE BP-02172 in a medium comprising a carbon source, to produce ergothioneine; and
   collecting the produced ergothioneine from the resulting culture.

15. The manufacturing method according to claim 14, wherein the medium comprises the carbon source with a concentration of from 0.1% to 5%.

16. The manufacturing method according to claim 14, wherein the medium further comprises an ammonium salt with a concentration of from 0.2 g/L to 2.0 g/L.

17. The manufacturing method according to claim 14, wherein the medium comprises ammonium chloride or ammonium dihydrogen phosphate as an ammonium salt.

18. The manufacturing method for ergothioneine according to claim 1, wherein the budding yeast is the *Rhodotorula mucilaginosa*.

* * * * *